United States Patent
Mukouyama et al.

(12)

(10) Patent No.: US 6,821,760 B1
(45) Date of Patent: Nov. 23, 2004

(54) METHODS FOR PRODUCING L-ASPARTIC ACID

(75) Inventors: Masaharu Mukouyama, Ibaraki (JP); Shinzo Yasuda, Ibaraki (JP); Satomi Komatsuzaki, Ibaraki (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/408,142

(22) Filed: Sep. 29, 1999

(30) Foreign Application Priority Data

Sep. 30, 1998 (JP) ............................................ 10-278571
Sep. 30, 1998 (JP) ............................................ 10-278579

(51) Int. Cl.$^7$ ................................................ C12P 13/20
(52) U.S. Cl. ...................................... 435/109; 562/571
(58) Field of Search .......................... 435/109; 562/571

(56) References Cited

U.S. PATENT DOCUMENTS

| 4,900,821 A | * | 2/1990 | Tan et al. .................... 540/540 |
| 5,488,155 A | | 1/1996 | Brun et al. |
| 5,530,160 A | | 6/1996 | Nore et al. |

FOREIGN PATENT DOCUMENTS

| EP | 0 588 674 A1 | 8/1993 |
| EP | 0 678 499 A1 | 4/1995 |
| EP | 0 952 225 A2 | 11/1999 |
| JP | 46-92844 | 11/1971 |
| JP | 07308195 A | 11/1995 |
| JP | 07313178 A | 12/1995 |
| JP | 08033492 A | 2/1996 |
| JP | 08033493 A | 2/1996 |
| JP | 09322790 A | 12/1997 |

OTHER PUBLICATIONS

Pavia et al., "Introduction to Organic Laboratory Techniques", 1976, p. 514., Saunders.*

* cited by examiner

Primary Examiner—Irene Marx
(74) Attorney, Agent, or Firm—Gray Cary Ware & Freidenrich, LLP

(57) ABSTRACT

This invention relates to a method for producing L-aspartic acid comprising treating an ammonium fumarate solution with aspartase to generate an ammonium L-aspartate solution; adding fumaric acid to the solution; and then crystallizing L-aspartic acid from the solution, wherein fumaric acid is added to the ammonium L-aspartate solution after the solution has been heated to 50 to 130° C. in an amount 0.4 to 0.8 times the total amount of fumarate and the L-aspartate contained therein in terms of mole, and the resultant mixture is once turned into a homogeneous solution by applying thereto a shearing force, and then L-aspartic acid is deposited therefrom, or wherein the solution is cooled at a rate of 0.1–5° C./min from the temperature at which fumaric acid is added thereto to the temperature at which crystallized L-aspartic acid is separated therefrom, to thereby deposit L-aspartic acid.

10 Claims, 2 Drawing Sheets

METHODS FOR PRODUCING L-ASPARTIC ACID

FIELD OF THE INVENTION

The present invention relates to methods for producing crystalline L-aspartic acid from fumaric acid using aspartase.

BACKGROUND OF THE INVENTION

Japanese Unexamined Patent Publication No. 48-56618 discloses a method for depositing and recovering D,L-aspartic acid by adding fumaric acid to a disodium D,L-aspartate solution. In this method, disodium fumarate and greatly excessive ammonia are chemically reacted to generate D,L-aspartic acid. After removal of excessive ammonia, fumaric acid is added to the reaction solution to thereby deposit the D,L-aspartic acid, which is then separated from the solution.

In this case, the solution to which fumaric acid is added is a disodium D,L-aspartate solution, and the filtrate obtained by adding fumaric acid to this disodium D,L-aspartate solution and then separating D,L-aspartic acid therefrom is a disodium fumarate solution. It is disclosed that the same reaction is repeated using this filtrate after addition of greatly excessive ammonia in relation to the amount of fumaric acid.

Usually, when L-aspartic acid is produced from diammonium fumarate using an enzyme, the amount of ammonia required is at least 1 time the amount of the raw material fumaric acid in terms of mole. In order to incline the equilibrium of reaction toward L-aspartic acid, usually ammonia is used 2 to 2.3 times the amount of fumaric acid in terms of mole. The optimum pH of aspartase, an enzyme which catalyzes this reaction, is around 8.3. In a pH range which is much higher than this value, various problems occur such as decrease of the enzyme activity or denaturation of the enzyme. Although greatly excessive ammonia is added to the disodium fumarate solution and used in repeated reactions in the method of Japanese Unexamined Patent Publication No. 48-56618, it is not possible to use greatly excessive ammonia in an aspartase enzyme reaction.

The pH of disodium fumarate solution (1.72 mol/l) is 8.4. However, when equimolar ammonia is added thereto, the pH of the resultant solution is 12.1 at 30° C. Aspartase will be denatured at such a pH level. Thus, ammonia cannot be used in enzyme reactions using aspartase.

Japanese Patent No. 2524306 discloses a method for depositing and recovering L-aspartic acid by adding fumaric acid to a monoammonium L-aspartate solution. In this method, a diammonium fumarate solution is converted into a monoammonium L-aspartate solution by the action of aspartase, and then fumaric acid is added thereto to deposit L-aspartic acid. After separation of the crystals, ammonia is added to the filtrate, which is then recycled in the subsequent reaction.

In the above method, a salt exchange reaction between L-aspartic acid and fumaric acid is performed by adding fumaric acid to the monoammonium L-aspartate solution under heterogeneous conditions in which fumaric acid crystals and/or L-aspartic acid crystals are constantly present. Since dissolution of fumaric acid and crystallization of L-aspartic acid occur simultaneously in this method, when L-aspartic acid is deposited as crystals, these crystals grow using undissolved fumaric acid crystals as a crystal nucleus. This has caused a problem that the mixed fumaric acid decreases the purity of the resultant L-aspartic acid. Furthermore, since fumaric acid is mixed in the resultant crystals as a crystal nucleus, it cannot be removed efficiently even if various washing operations such as resuspension of the crystals are carried out. In addition, the crystals deposited by this method are extremely small (several micrometers in size) and thus difficult to handle.

As described above, in the method for crystallizing L-aspartic acid by adding fumaric acid to an ammonium salt of L-aspartic acid, no effective method has been found to date in which L-aspartic acid, crystals are deposited from a reaction solution after the solution has been made completely homogeneous.

OBJECTS AND SUMMARY OF THE INVENTION

It is an object of the present invention to solve the problems described above and to provide a method for producing crystalline L-aspartic acid of higher purity using aspartase.

As a result of intensive and extensive researches toward the solution of the above problems, the present inventors have found that the purity of resultant L-aspartic acid crystals can be improved if fumaric acid is added to a preheated ammonium L-aspartate solution and once dissolved homogeneously prior to the deposition of L-aspartic acid.

Briefly, an ammonium fumarate solution is converted into an ammonium L-aspartate solution by the action of aspartase. This solution is heated to 50 to 130° C. Fumaric acid is added thereto in an amount 0.4 to 0.8 times the total amount of fumarate and L-aspartate contained therein in terms of mole, and agitated. Then, the fumaric acid is immediately dissolved and a homogeneous, crystal-free solution can be obtained. When this solution which has once become homogeneous is left standing or cooled, it is possible to deposit L-aspartic acid crystals alone. As to the crystal form, it is also possible to obtain needle-like crystals 100–1000 μm in average length by the above procedures.

Thus, if the ammonium L-aspartate solution is preheated, fumaric acid added thereto is immediately dissolved to yield a homogeneous solution. As a result, the contamination of L-aspartic acid crystals with fumaric acid crystals can be prevented.

The inventors have also found that the purity of resultant L-aspartic acid crystals can be improved if, after the addition of fumaric acid to an ammonium L-aspartate solution, L-aspartic acid is deposited by cooling the solution at a rate of 0.1 to 5° C. per minute.

It was found that highly pure L-aspartic acid crystals can be obtained by those methods. Thus, the present invention has been achieved.

The present invention encompasses the following inventions.

(1) A method for producing L-aspartic acid comprising treating an diammonium fumarate solution with aspartase to generate an ammonium L-aspartate solution; adding fumaric acid to the solution; and then crystallizing L-aspartic acid from said solution, wherein fumaric acid is added to the ammonium L-aspartate solution after the solution has been heated to 50 to 130° C. in an amount 0.4 to 0.8 times the total amount of fumarate and the L-aspartate contained therein in terms of mole, and the resultant mixture is once turned into a homogeneous solution by applying thereto a shearing force, and then L-aspartic acid is deposited therefrom.

(2) The method of (1) above, wherein the temperature of resultant suspension containing L-aspartic acid crystals is in the range from 25 to 100° C. when the deposited L-aspartic acid is separated therefrom.

(3) The method of (1) above, wherein the homogeneous solution is retained at 50 to 130° C. for 0.1 second to 1 hour.

(4) The method of (1) above, wherein moisture-containing fumaric acid crystals and the ammonium L-aspartate solution are mixed continuously.

(5) The method of (1) above, wherein the solution is cooled at a rate of 0.1–5° C./min from the temperature at which fumaric acid is added thereto to the temperature at which crystallized L-aspartic acid is separated therefrom, to thereby deposit L-aspartic acid.

(6) The method of (5) above, wherein the cooling is performed by evaporating water under reduced pressure; condensing the evaporated water by cooling through a condenser; and returning the condensed water to a reactor for L-aspartic acid crystallization or removing the condensed water.

(7) The method of (6) above, wherein pressure reduction at the time of cooling under reduced pressure is performed at a rate of 1–20 torr/min from a range of pressure 10–200 torr higher than the vapor pressure at which the solution to be cooled begins to boil.

(8) The method of (1) above, wherein the crystallizing step is performed by a continuous method.

(9) The method of (1) above, wherein a said ammonium fumarate solution is prepared from a mother liquor from which L-aspartic acid crystals have been removed.

(10) A method for producing L-aspartic acid comprising treating an diammonium fumarate solution with aspartase to generate an ammonium L-aspartate solution; adding fumaric acid to the solution; and then crystallizing L-aspartic acid from the solution, wherein the solution is cooled at a rate of 0.1–5° C./min from the temperature at which fumaric acid is added thereto to the temperature at which crystallized L-aspartic acid is separated therefrom, to thereby deposit L-aspartic acid.

(11) The method of (10) above, wherein the solution from which L-aspartic acid is deposited is a homogeneous solution.

(12) The method of (10) above, wherein the cooling is performed by evaporating water under reduced pressure; condensing the evaporated water by cooling through a condenser; and returning the condensed water to a reactor for L-aspartic acid crystallization or removing the condensed water.

(13) The method of (12) above, wherein pressure reduction at the time of cooling under reduced pressure is performed at a rate of 1–20 torr/min from a range of pressure 10–200 torr higher than the vapor pressure at which the solution to be cooled begins to boil.

(14) The method of (10) above, wherein a said ammonium fumarate solution is prepared from a mother liquor from which L-aspartic acid crystals have been removed.

The first invention of the present application is a method for producing L-aspartic acid comprising treating an diammonium fumarate solution with aspartase to generate an ammonium L-aspartate solution; adding fumaric acid to the solution; and then crystallizing L-aspartic acid from said solution, wherein fumaric acid is added to the ammonium L-aspartate solution after the solution has been heated to 50 to 130° C. in an amount 0.4 to 0.8 times the total amount of fumarate and the L-aspartate contained therein in terms of mole, and the resultant mixture is once turned into a homogeneous solution by applying thereto a shearing force, and then L-aspartic acid is deposited therefrom.

The second invention of the present application is a method for producing L-aspartic acid comprising treating an diammonium fumarate solution with aspartase to generate an ammonium L-aspartate solution; adding fumaric acid to the solution; and then crystallizing L-aspartic acid from the solution, wherein the solution is cooled at a rate of 0.1–5° C./min from the temperature at which fumaric acid is added thereto to the temperature at which crystallized L-aspartic acid is separated therefrom, to thereby deposit L-aspartic acid.

As to the aspartase used for the present invention, a transformant containing a transferred aspartase gene or such a transformant treated and immobilized may be used.

In the above-described method in which a liquid mixture of diammonium fumarate and ammonium L-aspartate containing 5–25% of fumarate and L-aspartate (as calculated for fumaric acid) is fed to a reactor containing an immobilized aspartase having activity of 250 U/ml or more, the liquid feeding rate is preferably in the range from 2 to 25 in terms of LHSV (liquid hourly space velocity).

In the present specification, the following terms have the following meanings:

1 U means production of 1 μmol of L-aspartic acid/min/ml immobilized enzyme

LHSV (liquid hourly space velocity) means liquid fed (ml)/catalyst packed (ml)/hr Specific examples of immobilized aspartases useful in the present invention include one which is prepared by immobilizing cells or a material obtained from treated cells on an ion exchange resin as a carrier by adsorption or coating with a polymer.

More specifically, an immobilized aspartase prepared as described below may be used. Briefly, a spherical styrene-divinylbenzene copolymer ion exchange resin is selected as an immobilization carrier. A polymer represented by formula (I):

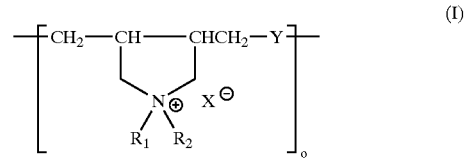

(wherein Y is a direct linkage or a divalent group represented by one of the formulas below; $R_1$ and $R_2$ are independently hydrogen or an organic residue; $X^{\ominus}$ is an anion; and n is an integer from 100 to 5000)

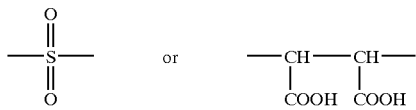

is mixed with cells or a material obtained from treated cells. Then, this mixture is coated on the surface of the spherical styrene-divinylbenzene copolymer ion exchange resin for immobilization.

In formula (I) above, specific examples of the organic residue represented by $R_1$ or $R_2$ include alkyl groups with 10 or less carbon atoms such as methyl, ethyl, n-propyl, isopropyl, n-butyl, isobutyl and tert-butyl. Particularly preferable is methyl. Further, an organic residue having a substituent such as halogen or hydroxyl may also be used.

Specific examples of such organic residues include 4-chloro-2,2-dimethylpentyl, 3-ethyl-2,5-dichloroheptyl and 2-hydroxy-3,5-dimethylnonyl. Preferably, 3-chloro-2-hydroxypropyl may be used. As to the anion, a halogen ion such as $F^-$, $Cl^-$, $Br^-$ and $I^-$ may be used, for example.

This specification includes part or all of the contents as disclosed in the specifications and/or drawings of Japanese Patent Application Nos. 10-278571 and 10-278579, which are priority documents of the present application.

BRIEF DESCRIPTION OF THE DRAWINGS

In FIG. 1, (A) is a line mixer with jacket.

In FIG. 2, (A) is a separable flask equipped with an agitator in which a 50% by weight fumaric acid slurry is prepared, (B) is a plastic tank containing aqueous ammonium L-aspartate solution, (C) and (D) are respectively pumps, (E) and (F) are respectively stainless pipes, (G) is a static mixer equipped with a jacket in which a heat medium of 95° C. is circulating, (H) is a separable flask equipped with an agitator (crystallizer), (I) is a condenser, (J) is a receiver, (K) is a slurry-drawing out vessel in which the pressure is reduced to 30 torr in advance, and (L) is a thermostatic bath (100° C.)

DETAILED DESCRIPTION OF THE INVENTION

Figure 1:
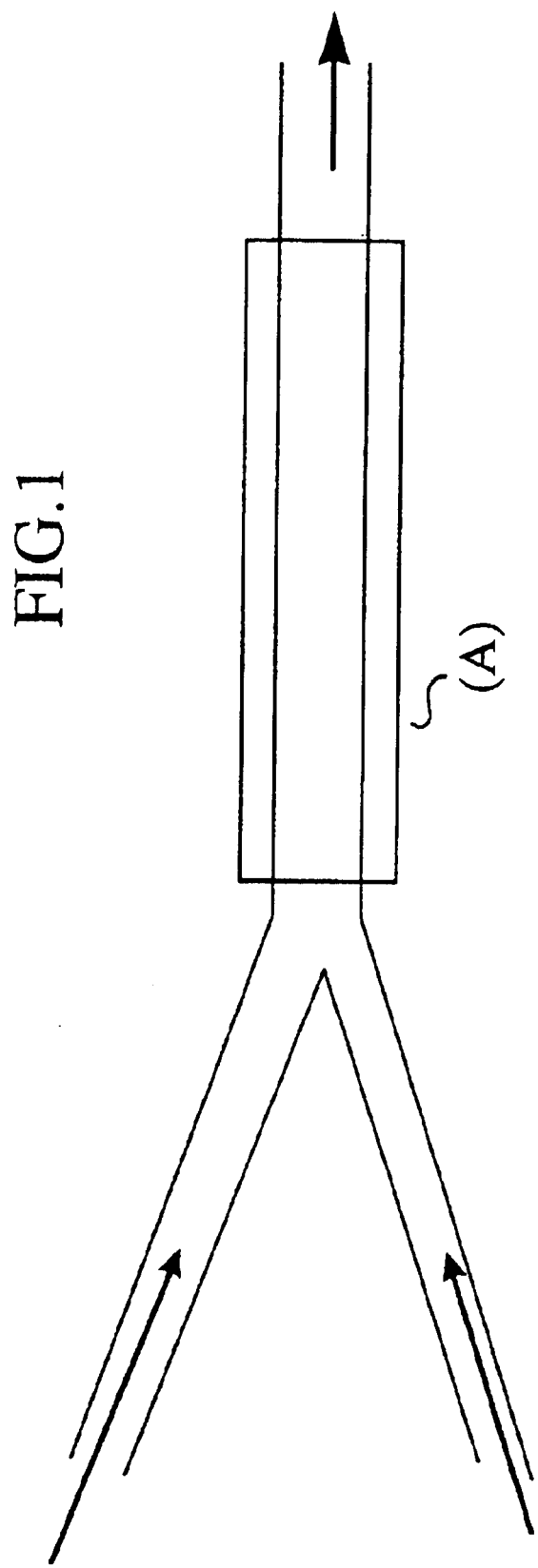
FIG. 1 shows an outline of a specific apparatus for preparing a homogeneous solution using a continuous mixing tube.

Hereinbelow, the present invention will be described in detail.

The enzyme-containing material with aspartase activity for use in the present invention may be selected, for example, from the following materials: cells of a microorganism such as *Escherichia coli*, a bacterium belonging to the genus Brevibacterium or Pseudomonas that is known to have high aspartase activity; disrupted cells of such a microorganism obtained by sonication, grinding, freeze-thawing, enzyme treatment, detergent treatment, etc.; a partially purified aspartase obtained by treating the disrupted cells by conventional methods such as ammonium sulfate salting out or acetone precipitation; or a purified aspartase obtained by further treating by conventional methods such as chromatography. Any of these materials may be used. For a purpose of enhancing productivity, it is preferable to use, as cells with aspartase activity, those *E. coli* cells which have been transformed with an aspartase gene-incorporating plasmid and have acquired an ability to produce a remarkable amount of aspartase. Specific examples of aspartase genes useful in the present invention include *E. coli*-derived aspartase genes; *Psuedomonas fluorescens*-derived aspartase genes; and aspartase genes derived from such microorganisms as bacteria belonging to the genus Enterobacter or Citrobacter that are known to be genetically crossing with *E. coli* in nature and have aspartase activity. Such a gene may be obtained from the genomic DNA of, for example, *E. coli* K-12 (IFO3301) or *Psuedomonas fluorescens* (IFO3081) by PCR amplification using primers designed based on a known aspartase gene sequence.

The plasmid into which the aspartase gene is to be inserted is not particularly limited as long as it is replicable in cells of microorganisms belonging to *E. coli* For example, pUC18, pUC19 or pKK223-3 may be used. As to the host microorganism into which the aspartase gene-inserted plasmid is to be introduced, *E. coli* K-12 strain is preferable. These microorganism cells with aspartase activity, a material obtained by treating such cells or an aspartase enzyme from such cells may also be used in an immobilized form.

As a carrier for immobilization, a natural polymer such as cellulose, alginic acid, carrageenan, mannan gel; or a synthetic polymer such as ion exchange resin, polyvinyl alcohol, polyacrylamide may be used according to conventional methods. Particularly preferable is a spherical styrene-divinylbenzene copolymer ion exchange resin. An immobilized aspartase is preferable which is obtained by mixing a polymer represented by formula (I) above with microorganism cells or a material from treated cells and coating the above ion exchange resin with the resultant mixture for immobilization.

The immobilized aspartase thus prepared has a small pressure loss and a small diffusion resistance since its diffusion layer is thin. Therefore, it can be used in a reaction performed at a high LHSV.

The substrate used in the present invention is an diammonium fumarate solution, i.e. an aqueous solution of a neutralization salt between fumaric acid and ammonia. The amount of ammonia used for the neutralization is not particularly limited. Preferably, this amount is 1.8 to 2.8 times, more preferably 2.0 to 2.4 times the amount of fumaric acid contained in the substrate solution in terms of mole. The pH of the substrate solution is not particularly limited. Preferably, the pH is 6 to 11, more preferably 7 to 10, most preferably 7.5 to 9.5 at 25° C.

Usually, the fumaric acid concentration in the reaction is preferably 5 to 25% by weight. Considering productivity, the purity of resultant L-aspartic acid and the solubility of fumarates, a concentration range from 12 to 25% by weight will be particularly effective.

It is desirable to add to the substrate medium a divalent metal salt such as a manganese salt (e.g. manganese chloride, manganese sulfate), a magnesium salt (e.g. magnesium chloride, magnesium sulfate) or a cobalt salt at a concentration of preferably 0.1–50 mM, more preferably 1–10 mM.

Embodiments of a reactor for use in the present invention are not particularly limited. A conventional reactor e.g. a batch-type reaction apparatus or column-type reaction apparatus may be used. Either a single reactor or a combination of reactors may be used. For industrial mass production, a column-type reaction apparatus is especially preferable. When an immobilized aspartase prepared by mixing a polymer represented by formula (I) above with *E. coli* cells which have been transformed with an aspartase gene-incorporating plasmid and have acquired an ability to produce a remarkable amount of aspartase, and coating the above-mentioned styrene-divinylbenzene copolymer ion exchange resin with the resultant mixture is used in such an apparatus, a reaction can be performed at a liquid feeding rate of LHSV=2–25. When conventional *E. coli* cells are used in an immobilized form, it is necessary to prolong the reaction time or reduce the liquid feeding rate since such cells have rather low aspartase activity. In contrast, since the transformant-immobilized aspartase described above has very high activity, a sufficient conversion ratio can be achieved even at the above-mentioned liquid feeding rate. As to the reaction temperature, preferably the lower limit is 10° C. because the reaction rate decreases at low temperatures. The upper limit is preferably 50° C. because aspartase is deactivated at high temperatures. More preferably, the reaction is performed at 15–40° C.

Under the above-described conditions, an ammonium fumarate solution is subjected to an enzyme reaction using aspartase to thereby convert the above solution into an ammonium L-aspartate solution. Although higher conversion ratios are desirable, a ratio around 90% will be sufficient for the subsequent crystallization of L-aspartic acid even if not reaching the equilibrium.

Then, in the first invention of the present application, the thus obtained reaction solution is heated to 50° C. or above. There is no definite upper limit temperature for this heating. However, around 130° C. at which no problems such as quality change of the reaction solution occur should be made the limit. If the temperature of the heated reaction solution is too low, fumaric acid to be added thereto will not dissolve homogeneously and L-aspartic acid crystals contaminated with fumaric acid crystals will deposit, reducing the purity. If the temperature of the heated solution is much higher than 130° C., the quality of the solution will change or it will become necessary to use a highly pressure resisting apparatus. Subsequently, fumaric acid is added to the heated reaction solution. As to the amount of this fumaric acid in relation to the total amount of fumaric acid and L-aspartic acid contained in the reaction solution, the lower limit is 0.4 times or more, preferably 0.45 times or more, and the higher limit is 0.8 times or less, preferably 0.6 times or less, in terms of mole. If the amount of addition is below 0.4 times in terms of mole, the amount of L-aspartic acid which can be separated as crystals will become small. If the amount of addition is above 0.8 times in terms of mole, the added fumaric acid will not dissolve homogeneously and the resultant L-aspartic acid will be contaminated with fumaric acid or a salt thereof, reducing the purity of the L-aspartic acid.

The fumaric acid to be added may take any of the following forms: dry crystals, moisture-containing crystals, aqueous suspension or the like. Considering a burden for a process, in particular, dry crystals containing below 0.5% of water are advantageous. Since they make a burden smaller in concentrating a filtrate which is left after separation of crystals. Considering convenience for handling, in particular, moisture-containing crystals are advantageous. Since they do not contain dust and they are easily mixed with the heated reaction solution, the time required for dissolution can be made shorter. As to the moisture content of such moisture-containing crystals in relation to the moisture-containing crystals, the lower limit is preferably 0.5% by weight or more, more preferably 3% by weight or more, and the higher limit is preferably 40% by weight or less, more preferably 10% by weight or less. If the moisture content is below 0.5% by weight, there will arise a possibility that fumaric acid dust may occur. If the moisture content is above 40% by weight, it will become difficult to handle such crystals as powder. Use of aqueous suspension of fumaric acid is preferable from the viewpoint of industrial production since it can be added to the reaction solution with a pump as a slurry. As to the moisture content of such aqueous suspension of fumaric acid in relation to the amount of fumaric acid, the lower limit is preferably 50% by weight or more, more preferably 60% by weight or more, and the higher limit is preferably 200% by weight or less, more preferably 150% by weight or less. If the moisture content is below 50% by weight, fluidity will decrease and thus it will become difficult to add such a suspension with a pump as a slurry. If the moisture content is above 200% by weight, the amount of water to be condensed during the recycling of the reaction solution will increase. Prior to addition, it is preferable to heat moisture-containing fumaric acid crystals or aqueous suspension of fumaric acid to the same temperature as that of the heated reaction solution described above. This facilitates the dissolution of fumaric acid in the reaction solution.

Figure 2:
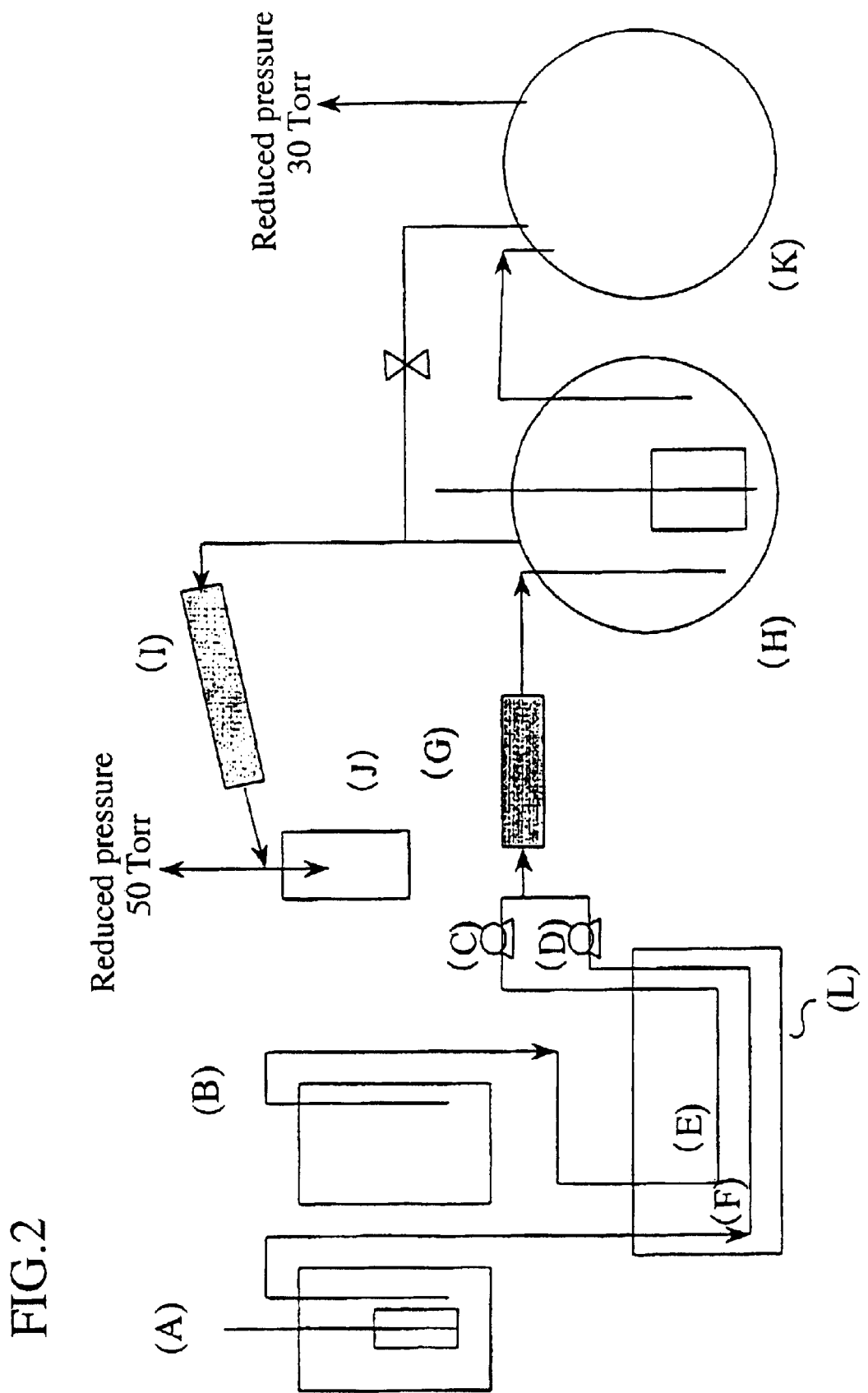
FIG. 2 shows an outline of a Continuous Crystallizer.

In the first invention of the present application, to the reaction solution to which fumaric acid has been added, a shearing force is applied at 50 to 130° C. to allow dissolution of the fumaric acid. Specifically, a shearing force can be applied thereto by strongly agitating and mixing the solution. By this operation, the reaction solution is turned into a homogeneous solution in which neither fumaric acid crystals nor L-aspartic acid crystals are present. As to the method for applying a shearing force, a batch-type agitation vessel or a continuous mixing tube may be used, for example. As a continuous mixing tube, a line mixer such as a static mixer is preferable. The time required for mixing and dissolution is approximately 0.1 to several seconds for a line mixer, whereas the time is approximately 1 to 10 minutes for an agitation vessel. When an aqueous suspension of fumaric acid is used in the addition of fumaric acid, it is preferable to use an apparatus as shown in FIG. 2 since continuous dissolution can be carried out with such an apparatus.

Upon dissolution of the fumaric acid, the temperature of the reaction solution is preferably retained for 0.1 second to 1 hour. In some cases, L-aspartic acid crystals begin to deposit by this operation. At this time, the mole ratio of (fumaric acid+L-aspartic acid):ammonia is 1.1:1 to 1.8:1. The amount of ammonia is less than the amount necessary to neutralize L-aspartic acid and fumaric acid. Under such conditions, fumaric acid crystals and L-aspartic acid crystals are not completely neutralized with ammonia. Therefore, under conventional conditions, they do not dissolve completely. As fumaric acid dissolves, L-aspartic acid which is dissolving by forming a pairing salt with an ammonium ion is deprived of the ammonium ion by fumaric acid and begins to deposit as L-aspartic acid crystals. However, if the reaction solution is preheated and the dissolution of added fumaric acid is performed rapidly, a homogeneous solution in which neither fumaric acid crystals nor L-aspartic acid crystals are present can be obtained. Further, the purity of L-aspartic acid to be deposited later can also be improved by the above operations.

The deposition of L-aspartic acid crystals can be performed by allowing to stand or cooling the above-described reaction solution under agitation. These operations can be performed by known methods. For example, these operations may be performed as follows. First, 1 L of 23% ammonium L-aspartate solution (pH 8.5 at 25° C.) is heated to 95° C. Fumaric acid (100 g) is added to this solution and agitated strongly. Then, the solution once becomes a homogeneous solution. When this solution is allowed to stand under agitation, a small amount of L-aspartic acid microcrystals begin to deposit in about 3 minutes and the solution becomes translucent. When agitation is continued further for 30 minutes, the deposition of L-aspartic acid crystals proceeds and the solution becomes opaque as a whole. When this solution is cooled further, L-aspartic acid crystals deposit in large quantity.

In another embodiment of the invention, 1 L of 23% ammonium L-aspartate solution (pH 9.5 at 25° C.) is heated to 95° C. Fumaric acid (100 g) is added to this solution and agitated strongly. Then, the solution once becomes a homogeneous solution. Crystals do not deposit even when this solution has been allowed to stand for 30 minutes under agitation. When this solution is cooled, it becomes translucent at around 83° C. and L-aspartic acid microcrystals begin to deposit. When this solution is cooled further, L-aspartic acid crystals deposit.

In the second invention of the present application, as to the cooling rate at this time, the lower limit is 0.1° C./min or more, preferably 0.2° C./min or more, and the higher limit is 5° C./min or less, preferably 3° C./min or less. If the rate is faster than 5° C./min, not only the purity of deposited L-aspartic acid will decrease but also the crystal size will become smaller to make the handling difficult. If the cooling rate is slower than 0.1° C./min, it will take a long time for cooling to make the productivity worse. If necessary, the cooling rate can be regulated, as long as it is in the range described above.

As a method for cooling the reaction solution, usually, a method using an agitation vessel is employed. For example, a method in which the solution is cooled in a jacket; a method in which water is vaporized under reduced pressure, condensed in a condenser, and returned to an agitation vessel or removed, to thereby deprive the solution of the heat of evaporation; and the like may be used. In particular, the method of cooling by deprivation of the heat of vaporization is industrially advantageous because L-aspartic acid crystals do not adhere to cooled surfaces and, thus, cooling can be performed efficiently.

The rate of pressure reduction during cooling performed by the above method utilizing the heat of vaporization is 1 torr/min or more, preferably 2 torr/min or more, and 20 torr/min or less, preferably 10 torr/min or less. This pressure reduction starts from the pressure which is higher than the vapor pressure at which the fumaric acid-added liquid begins to boil, by 10 torr or more, preferably 50 torr or more, and 200 torr or less, preferably 100 torr or less. If the rate of pressure reduction is slower than 1 torr/min, a long time will be required for cooling. If the rate is faster than 20 torr/min, bumping of the fumaric acid-added solution may occur and the size of the deposited crystals will become too small. When crystals become too small, the crystal size may be as small as several micrometers. This will make separation of crystals and subsequent handling difficult.

The fumaric acid-added liquid is cooled to preferably 25° C. or more, more preferably 30° C. or more, preferably 100° C. or less, more preferably 80° C. or less, most preferably 60° C. or less. After completion of this cooling, the liquid is preferably retained at that temperature for 1 minute to 1 hour to thereby complete the deposition of L-aspartic acid crystals. The form of the thus deposited L-aspartic acid crystals is mainly a needle-like form 30–1000 μm in average length. When they are subjected to filtration, liquid passes through them quickly. Thus, their purity can be improved by simple washing operations.

As to a method for separating deposited L-aspartic acid crystals, a conventional method such as vacuum filtration or centrifugal filtration may be used. Preferably, centrifugal filtration which can reduce the moisture content of crystals is used. Centrifugal filtration can reduce the moisture content of separated L-aspartic acid crystals to about 5–30% though the results vary depending on the capacity of a centrifuge used. Thus, highly pure L-aspartic acid crystals can be obtained.

The separated L-aspartic acid crystals are washed with water if necessary. If washing is not performed, the purity of the L-aspartic acid will be 98–99% by weight. By washing, the amount of fumaric acid mixed slightly in L-aspartic acid crystals can be reduced, and the purity of the resultant L-aspartic acid crystals can be made 99% by weight or more constantly. Thus, it is preferable to perform washing. However, considering reuse of the mother liquor from which crystals have been removed, it is not desirable to wash crystals with a large quantity of water. The amount of washing water used is 2% by weight or more, preferably 4% by weight or more, more preferably 8% by weight or more, and 200% by weight or less, preferably 100% by weight or less, more preferably 50% by weight or less, in relation to the amount of L-aspartic acid crystals.

When crystallization steps are performed continuously, it is also possible to obtain larger crystals by feeding a homogeneously dissolved solution, or a liquid in which crystals have partially begun to deposit, into a crystallization slurry vessel, the temperature of which is pre-adjusted to a scheduled temperature, to thereby allow the growth of L-aspartic acid crystals in the crystallization slurry vessel. In this case, the cooling may be performed by a method in which water is evaporated under reduced pressure, a method in which jackets, cooling coils, etc. are used, or the like. Especially preferable is the method in which water is evaporated under reduced pressure to deprive the solution of the heat of evaporation. As a method for feeding a homogeneously dissolved solution into a pressure-reduced vessel, for example, a method in which an orifice or the like is provided so that the solution undergoes resistance before entering the vessel, or a method in which the slurry is circulated from the crystallization slurry vessel and the solution is introduced into this line is especially preferable. According to such a method, a solution somewhat supersaturated with L-aspartic acid can be generated constantly. As a result, deposited crystals are easy to grow. A feeding rate of the homogeneously dissolved solution does not have to be controlled, as long as a fed liquid is cooled enough to keep the temperature within the crystallization slurry vessel, preferably 25° C. or more, more preferably 30° C. or more, preferably 100° C. or less, more preferably 80° C. or less, most preferably 60° C. or less. In continuous crystallization, the residence time of the crystallization slurry is at least 1 minute or more, preferably 10 minutes or more, more preferably 30 minutes or more; and is at the maximum 10 hours or less, preferably 5 hours or less, more preferably 2 hours or less.

Thus, L-aspartic acid containing a small amount (e.g. 0.05–2% by weight, preferably 0.1–1% by weight) of fumarate can be obtained by a simple method. These crystals containing fumarate are easy to handle since they do not scatter easily even after drying. Hence, they are extremely useful as industrial L-aspartic acid. If purified further through repeated purification steps, this L-aspartic acid may be used as a food additive or used in the production of pharmaceuticals.

The mother liquor from which L-aspartic acid has been separated can be recycled as a substrate solution for L-aspartic acid production. Briefly, the mother liquor is mixed with the above-described washing liquid. Then, fumaric acid and ammonia are added thereto to re-prepare a substrate solution. In the above process, appropriate adjustment such as concentration of the mother liquor and/or the washing liquid is performed if necessary. For example, since the volume of the re-prepared substrate solution is larger than the volume of the initial substrate solution due to the washing liquid and aqueous ammonia added thereto, the mother liquor and/or the washing liquid can be concentrated so that the re-prepared solution will have the same volume as that of the initial substrate solution after the addition of aqueous ammonia.

The amount of fumaric acid to be added may be the amount obtained by subtracting the number of moles of the fumaric acid added for crystallization of L-aspartic acid from the number of moles of the L-aspartic acid separated as crystals. The amount of ammonia may be equal to the amount of the L-aspartic acid separated as crystals in terms of mole. By selecting these amounts, it is possible to achieve the following ratio in the solution:

(Total number of moles of fumaric acid+L-aspartic acid):(Total number of moles of ammonia+L-aspartic acid)=1:1.5–2.5

At this time, the pH of the solution is in the range from 7.5 to 9.5 at 25° C.

Specifically, the mother liquor from which L-aspartic acid has been removed is mixed with the washing liquid. To this mixture, the above-mentioned amount of fumaric acid is added. The resultant mixture is subjected to heating and pressure reduction to remove excessive water for concentration. Then, the above-mentioned amount of ammonia is added thereto to re-prepare a raw material solution for L-aspartic acid production.

By using the thus re-prepared substrate solution, an enzyme reaction using an enzyme-containing material with aspartase activity, heating, addition of fumaric acid, deposition of L-aspartic acid crystals by cooling, separation of the crystals and re-preparation of the mother liquor are repeated. Thus, the mother liquor is recycled as a substrate solution. According to the present invention, the mother liquor can be recycled 10 times or more.

When this recycling proceeds, the reaction solution turns into light yellow. It is possible to prevent the accumulation of coloring substances by purging a part of the reaction solution after completion of the reaction using an enzyme-containing material, if necessary. As to the amount of the reaction solution to be purged in relation to the total reaction solution, the lower limit is 1% or more, preferably 3% or more, more preferably 5% or more, and the higher limit is 20% or less, preferably 10% or less. The L-aspartic acid contained in the purged portion of the reaction solution can be recovered by a conventional crystallization/separation method using a mineral acid such as sulfuric acid. In order to prevent the accumulation of coloring substances in the reaction solution, conventional methods such as treatment of the solution with active carbon may also be used.

EFFECT OF THE INVENTION

According to the present invention, it is possible to produce highly pure, crystalline L-aspartic acid with an excellent operation efficiency without complicated steps.

DESCRIPTION OF THE PREFERRED EMBODIMENTS

Hereinbelow, the present invention will be described more specifically with reference to the following Examples, which should not be construed as limiting the technical scope of the invention.

Preparation Example 1

A method for preparing an *E. coli*-derived aspartase by recombinant DNA techniques will be described.

(i) Preparation of a Recombinant *E. coli* Aspartase

*Escherichia coli* IFO3301 strain purchased from Institute for Fermentation, Osaka (Japan) was inoculated into LB medium shown in Table 1 and cultured at 37° C. for 8 hours. Cells were harvested from 1 ml of the resultant culture fluid and suspended in 1 ml of distilled water. This cell suspension (1 µl) was used as a template DNA to amplify the aspartase gene of this *E. coli* strain.

TABLE 1

| Composition of LB Medium | |
| --- | --- |
| Polypeptone | 10 g |
| Yeast extract | 5 g |
| NaCl | 10 g |
| Distilled water | 1 L |

Autoclave-sterilized at 121° C. for 15 min.

(ii) Amplification of the Aspartase Gene by PCR and Preparation of an Insert

In order to amplify the aspartase gene of the above *E. coli* strain, the following two primers were prepared based on the known sequence (SEQ ID NO: 1) encoding the aspartase gene of *E. coli* K-12 strain (Biochem. J. 237 (2), 547–557).

Forward primer: GGATAATCGTCGGTCGAAAA (SEQ ID NO: 2)

Reverse primer: CGTCATCTGACGTGCCTTT (SEQ ID NO: 3)

A reaction solution having the composition shown in Table 2 was prepared using KOD DNA polymerase (Toyobo), and then the aspartase gene was amplified by PCR.

TABLE 2

| 10x Buffer | 5 µl |
| --- | --- |
| dNTPs Mix | 5 µl |
| MgCl$_2$ | 2 µl |
| Template DNA | 1 µl |
| KOD DNA polymerase | 1 µl |
| Forward primer (25 pmol) | 1 µl |
| Reverse primer (25 pmol) | 1 µl |
| Sterilized water | 34 µl |
| Total | 50 µl |

PCR Conditions

At 98° C. for 5 min and subsequently 30 cycles of at 98° C. for 30 sec; at 53° C. for 30 sec; and at 68° C. for 1 min.

After completion of the PCR reaction, amplified DNA fragments were electrophoresed on 1% agarose gel and stained with ethidium bromide. As a result, it was found that an expected fragment of about 1600 bp was amplified actually.

This fragment was cut out from the gel, and the DNA was recovered with Prep A Gene (BioRad).

(iii) Ligation of the Insert to a Vector

The DNA fragment recovered above (insert) was ligated to pCR-Script Amp SK(+) cloning vector in the presence of restriction enzyme Srf and DNA ligase.

One of the resultant transformants into which the above DNA fragment had been inserted was designated PUaspE1 clone. This clone was inoculated into 3 ml of LB medium supplemented with 100 ppm ampicillin and then cultured overnight at 37° C. under shaking. Subsequently, cells were harvested from 1.5 ml of the resultant culture liquid. The plasmid was recovered from these cells by the alkaline SDS method. This plasmid was designated pUaspE1.

The sequence of the insert in this plasmid was analyzed. As a result, it was found that the aspartase gene had been inserted in the opposite direction against the promoter of the vector. In order to re-ligate the insert in the same direction as that of the promoter, it was decided to cut out the insert from plasmid pUaspE1 using restriction enzymes SacI and BamHI and then introduce it into pUC19. Plasmid pUaspE1 was digested with restriction enzyme BamHI, followed by ethanol precipitation to recover the DNA. Subsequently, the DNA was digested with restriction enzyme SacI. The digested DNA fragment was separated by 1% agarose gel electrophoresis and cut out from the gel. Then, the DNA was recovered with Prep A Gene (BioRad).

(iv) Preparation of a Vector

Plasmid pUC19 (Nippon Gene) (1 µg) was digested with restriction enzyme BamHI, followed by ethanol precipitation to recover the DNA. Then, the DNA was digested with restriction enzyme SacI. The digested DNA fragment was separated by 1% agarose gel electrophoresis and cut out from the gel. Then, the DNA was recovered with Prep A Gene (BioRad) to thereby prepare a vector.

Ligation of the Insert to the Vector

The insert was ligated to the vector digested with the restriction enzymes using "Ligation High" (Toyobo) at 16° C. for 30 min.

(v) Transformation of E. coli

Two microliters of the resultant ligation solution was added to 200 µl of E. coli competent cells (XL 2-Blue MRF' Ultracompetent cells; Stratagene) to transform them. The transformed cells were spread on LB agar medium containing 100 ppm ampicillin and cultured overnight at 37° C.

As a control, E. coli competent cells were transformed with plasmid pUC19 not carrying the insert, and then spread on LB agar medium containing 100 ppm ampicillin and cultured overnight at 37° C. in the same manner.

Twenty colonies were picked up from the medium, inoculated into LB medium containing 100 ppm ampicillin and cultured at 37° C. under shaking. After 8 hours, IPTG (isopropylthio-β-D-galactoside) was added thereto to give a concentration of 1 mM. Then, the cells were cultured overnight at 30° C. under shaking. From 1 ml of the resultant culture liquid, the cells were harvested.

Likewise, one clone of the control transformant without the insert was cultured, and cells were harvested. To these harvested cells, 1 ml of the ammonium fumarate substrate solution shown in Table 3 was added to suspend the cells and reacted at 30° C. for 1 hr.

TABLE 3

| Composition of 20% Ammonium Fumarate Substrate Solution | |
|---|---|
| Fumaric acid | 200 g |
| 25% Aqueous ammonia | 200 g |
| $MgSO_4 \cdot 7H_2O$ | 2.5 g |
| Deionized water | 500 g |

The mixture was adjusted to pH 8.3 with 25% aqueous ammonia, and then deionized water was added thereto to make the volume 1 L.

The results of analysis of the reaction solution revealed that the ratio of conversion into L-aspartic acid was 99.5% when the E. coli transformant carrying the insert was used. On the other hand, when the control transformant not carrying the insert was used, the conversion ratio was 5%.

One of these transformants with insert was designated PUaspE2.

PUaspE2 was inoculated into 3 ml of LB medium supplemented with 100 ppm ampicillin and cultured at 37° C. for 8 hr. The plasmid was recovered from 1.5 ml of the resultant culture liquid by the alkaline SDS method. This plasmid was designated pUaspE2. Plasmid pUaspE2 was digested with restriction enzyme SmaI and subsequently with restriction enzyme HindIII, and then subjected to 1% agarose gel electrophoresis to determine the sizes of the resultant DNA fragments. As a result, it was found that two fragments of about 2960 bp and 1600 bp were present in the plasmid.

PUaspE2 clone was inoculated into 3 ml of LB medium supplemented with 100 ppm ampicillin and cultured at 37° C. under shaking. After 8 hours, IPTG (isopropylthio-β-D-galactoside) was added thereto to give a concentration of 1 mM. Then, the cells were cultured overnight at 30° C. under shaking. From 1 ml of the resultant culture liquid, the cells were harvested and their cell density (OD at 660 nm) was determined. As a result, OD660 was 8.0. These cells were suspended in 10 ml of 20% ammonium fumarate substrate solution and reacted at 30° C. for 1 hr. Subsequently, the reaction solution was analyzed by HPLC. The aspartase activity of these cells was calculated from the L-aspartic acid produced and the cell density. As a result, the aspartase activity was as follows: production of 2,000,000 µM L-aspartic acid/hr/OD660.

Similarly, one control clone without the insert was cultured; cells were harvested; and cell density (OD at 660 nm) was determined. As a result, OD660 was 8.5.

These control cells were suspended in 10 ml of 20% ammonium fumarate substrate solution and reacted at 30° C. for 1 hr. Subsequently, the reaction solution was analyzed by HPLC. Their aspartase activity was calculated from the L-aspartic acid produced and the cell density. As a result, the aspartase activity was as follows: production of 10,000 µM L-aspartic acid/hr/OD660. Thus, the obtained PUaspE2 strain had aspartase activity 200 times as high as that of the clone without inserted aspartase gene.

(vi) Cultivation of the Transformant

Transformant E. coli PUaspE2 clone into which the aspartase gene had been transferred was inoculated into 10 test tubes individually containing 3 ml of the medium shown in Table 1 supplemented with 100 ppm ampicillin, and cultured at 37° C. for 8 hr. Then, the resultant culture in each test tube was inoculated individually into a Sakaguchi flask containing 100 ml of the above-described medium supplemented with 1 mM IPTG. The cells were cultured overnight at 30° C. under shaking. The cells were harvested from the resultant culture liquid by centrifugation. The aspartase activity of these cells was measured and found to be as follows: production of 1.05 moles of L-aspartic acid/hr/g cells.

Preparation of Immobilized Aspartase Using the Transformant

Seventy grams of PAS-880 (Nitto Boseki) whose pH had been adjusted to around 7.0 with alkali and 230 g of deionized water were mixed thoroughly. The transformant cells harvested above were dispersed in this mixture uniformly. An ion exchange resin (Amberlite IRA-94SC1; Organo Corp.; mean particle size: 0.5 mm) (300 ml) and 0.5 in. Teflon balls (200 balls) were placed in a 6 L round-bottom flask, to which ⅙ of the cell suspension obtained above was added. Then, the resultant mixture was evaporated at 30° C. to dryness while rotating the flask, to thereby coat the ion exchange resin with the cells. This operation was repeated 6 times. Thereafter, the Teflon balls were removed to obtain bead-like, immobilized aspartase. The activity of this immobilized aspartase was 3500 U/ml (1 U=production of 1 µmol of L-aspartic acid/min/ml immobilized enzyme).

Cultivation of E. coli IFO3301 Strain

E. coli IFO3301 strain into which the aspartase gene had not been transferred was cultured in the same manner as described above except that ampicillin and IPTG were not added to the medium. Then, the cells were harvested.

Preparation of Immobilized Aspartase Using the Non-Transformant

Bead-like, immobilized aspartase was obtained in the same manner as described above except that E. coli IFO3301 strain was used. The activity of this immobilized aspartase was 180 U/ml (1 U=production of 1 μmol of L-aspartic acid/min/ml immobilized enzyme).

EXAMPLE 1

The transformant-immobilized aspartase prepared in Preparation Example 1 was dipped in 20% ammonium fumarate solution (pH 8.3) overnight. Subsequently, 500 ml of the resultant aspartase was packed in a column, outside of which was then covered with a heat insulator made of polystyrene foam to thereby insulate the reactor thermally. To this column, the substrate solution (shown in Table 4) retained at 20° C. in a thermostatic water bath of 20° C. was fed through a Teflon tube covered with a heat insulator at a rate of 5 L/hr (LHSV=10.0) and circulated to perform a continuous reaction.

TABLE 4

| Fumaric acid | 2.00 kg |
|---|---|
| 25% Aqueous ammonia | 2.34 kg |
| Magnesium sulfate | 25 g |

These components were dissolved in deionized water. After adjusting the pH of the solution to 8.5 at 25° C. with 25% aqueous ammonia, deionized water was added to make the volume 10 L.

The reaction solution was analyzed one hour after the start of the reaction. The results showed that L-aspartic acid was produced as a reaction product in an amount almost equimolar to that of the consumed fumaric acid, and that the ratio of conversion into L-aspartic acid was 99.2%.

Ten liters of this reaction solution (weight: 11.1 kg) was placed in a 20 L flask which was provided with a cooling tube so that pressure reduction and reflux could be carried out. The solution was heated to 95° C., and 1.0 kg of fumaric acid was added thereto and agitated. In about 2 minutes, the fumaric acid crystals were completely dissolved. Agitation was continued further. Then, in about 1 minute, crystals of L-aspartic acid began to deposit. After the liquid temperature was kept at 95° C. for 30 minutes, the pressure inside the flask was reduced at a rate of 15 torr/min. In the course of this operation, the liquid containing L-aspartic acid crystals began to boil at around 600 torr, thereafter the pressure was reduced while condensing the evaporated water in the cooling tube and returning it to the flask (average cooling rate: 0.24° C./min). After the pressure was reduced to 400 torr at which the liquid temperature was 78° C., the pressure was further reduced at a rate of 3 torr/min. About 2 hours thereafter, the pressure inside the flask was returned to ambient atmospheric pressure because the temperature of the liquid containing L-aspartic acid crystals reached 40° C. at 50 torr (average cooling rate: 0.33° C./min). Under these conditions, agitation was continued for 30 min to complete the deposition of L-aspartic acid crystals. The thus deposited L-aspartic acid crystals were separated through a centrifugal filter and washed with 1 L of water. The resultant L-aspartic acid crystals were 1.86 kg in weight (moisture content: 7.0%). After drying, the crystals had a weight of 1.73 kg and a purity of 99.7%. As to their form, they were mainly needle-like crystals 500 μm in average length. These L-aspartic acid crystals were suspended in 10 L of water, agitated and then subjected to centrifugal filtration to separate the L-aspartic acid crystals. The resultant L-aspartic acid crystals were 1.84 kg in weight (moisture content: 7.0%); after drying, the crystals had a weight of 1.71 kg and a purity of 99.9%.

The mother liquor from which the L-aspartic acid had been separated and the liquid which had washed the L-aspartic acid were combined, and 0.51 kg of fumaric acid was added thereto. This mixture was condensed by evaporating 2 kg of water with a rotary evaporator. To the resultant liquid, 885 g of 25% aqueous ammonia was added. Further, water was added thereto to make the total weight 11.1 kg. The pH of this liquid was 8.5 at 25° C.

Using another 10 L of the substrate solution shown in Table 4, the same operations as described above were performed to yield 1.89 kg (moisture content: 7.2%) of L-aspartic acid crystals. The purity of the resultant crystals was 99.6%. Likewise, the mother liquor and the washing liquid were combined, and 0.53 kg of fumaric acid was added to this mixture. After concentration, 25% aqueous ammonia was added thereto. The pH of the resultant liquid was adjusted to 8.5 at 25° C. Then, water was added thereto to make the total weight 11.1 kg. This liquid was combined with the re-prepared solution described above, kept in a thermostatic water bath of 20° C., fed to a column packed with the above-described transformant-immobilized aspartase through a Teflon tube covered with a heat insulator, and circulated at a rate of 5 L/hr (LHSV=10.0) to perform a continuous reaction. The reaction solution was analyzed one hour after the start of the reaction. The results showed that L-aspartic acid was produced as a reaction product in an amount almost equimolar to that of the consumed fumaric acid, and that the ratio of conversion into L-aspartic acid was 99.2%. Using 10 L of this reaction solution, the same operations as described above were performed to yield 1.86 kg (moisture content: 7.1%) of L-aspartic acid crystals. The purity of the resultant crystals was 99.7%. These operations were repeated further; the reaction solution of 20 L (taken as 1 unit) was re-prepared and used 5 times. The results are shown in Table 5 below.

TABLE 5

| Crystallization | 1st Time | 2nd Time | 3rd Time | 4th Time | 5th Time |
|---|---|---|---|---|---|
| Conversion ratio (%) | 99.2 | 99.2 | 99.3 | 99.2 | 99.2 |
| Wet L-aspartic acid crystals (kg) | 3.7 | 3.78 | 3.72 | 3.76 | 3.34 |
| Moisture content (%) | 7.0 | 7.1 | 7.4 | 7.2 | 7.1 |
| Dry weight (kg) | 3.49 | 3.51 | 3.4 | 3.49 | 3.47 |
| Purity (%) | 99.7 | 99.7 | 99.7 | 99.7 | 99.7 |
| Crystal form | needle-like | needle-like | needle-like | needle-like | needle-like |

Note: The values given above are calculated against 1 unit (i.e. 20 L) of reaction solution.

EXAMPLE 2

Heating and addition of fumaric acid were performed in the same manner as in Example 1 expect that fumaric acid wet crystals containing 5% moisture were used as the fumaric acid added for the crystallization of L-aspartic acid. When 1.06 kg of 5% moisture-containing fumaric acid was added to the reaction solution and agitated, the fumaric acid crystals were completely dissolved in about 30 seconds. When agitation was continued further, L-aspartic acid crystals began to deposit in about 3 minutes. After the reaction solution was cooled in the same manner as in Example 1, the L-aspartic acid crystals deposited were separated through a centrifugal filter and washed with 1 L of water. The resultant L-aspartic acid crystals were 1.85 kg in weight (moisture content: 7.0%). After drying, they had a weight of 1.72 kg and a purity of 99.7%. As to their form, they were mainly needle-like crystals 500 μm in average length.

EXAMPLE 3

The transformant-immobilized aspartase prepared in Preparation Example 1 was dipped in 20% ammonium fumarate solution (pH 9.5) overnight. Subsequently, 50 ml of the resultant aspartase was packed in a column, outside of which was then covered with a heat insulator made of polystyrene foam to thereby insulate the reactor thermally. To this column, the substrate solution (shown in Table 6 below) retained at 20° C. in a thermostatic water bath of 20° C. was fed through a Teflon tube covered with a heat insulator at a rate of 5 L/hr (LHSV=10.0) and circulated to perform a continuous reaction.

TABLE 6

| | |
|---|---|
| Fumaric acid | 2.00 kg |
| 25% Aqueous ammonia | 2.34 kg (2.0 times the amount of fumaric acid in terms of mole) |
| Magnesium sulfate | 25 g |

These components were dissolved in deionized water. After adjusting the pH of the solution to 9.5 at 25° C. with 25% aqueous ammonia, deionized water was added to make the volume 10 L.

The reaction solution was analyzed one hour after the start of the reaction. The results showed that L-aspartic acid was produced as a reaction product in an amount almost equimolar to that of the consumed fumaric acid, and that the ratio of conversion into L-aspartic acid was 99.7%.

Ten liters of this reaction solution (weight: 11.1 kg) was placed in a 20 L flask which was provided with a cooling tube so that pressure reduction and reflux could be carried out. The solution was heated to 95° C. When 1.00 kg of fumaric acid was added thereto and agitated, the fumaric acid crystals were completely dissolved. Even when agitation was continued further for 30 minutes, L-aspartic acid crystals did not form, and the solution remained homogeneous. After the solution temperature was retained at 95° C. for 30 minutes, the pressure inside the flask was reduced at a rate of 10 torr/min. In the course of this operation, the solution began to boil at around 600 torr, thereafter the pressure was reduced while condensing the evaporated water in the cooling tube and returning it to the flask (average cooling rate: 0.47° C./min). In this course, L-aspartic acid crystals began to deposit at around 83° C. of the liquid temperature. After the pressure was reduced to 400 torr at which the liquid temperature was 78° C., the pressure was further reduced at a rate of 3 torr/min. About two hours thereafter, the pressure inside the flask was returned to ambient atmospheric pressure because the temperature of the liquid containing L-aspartic acid crystals reached 40° C. at 50 torr (average cooling rate: 0.33° C./min). Under these conditions, agitation was continued for 30 minutes to complete the deposition of L-aspartic acid crystals. The thus deposited L-aspartic acid crystals were separated through a centrifugal filter and washed with 1 L of water. The resultant L-aspartic acid crystals were 1.68 kg in weight (moisture content: 7.0%). After drying, the crystals had a weight of 1.56 kg and a purity of 99.7%. As to their form, they were mainly needle-like crystals 700 μm in average length.

The mother liquor from which the L-aspartic acid had been separated and the liquid which had washed the L-aspartic acid were combined, and 160 g of fumaric acid was added thereto. This mixture was condensed by evaporating 2 kg of water with a rotary evaporator. To the resultant liquid, 680 g of 25% aqueous ammonia was added. Further, water was added thereto to make the total weight 11.1 kg. The pH of this liquid was 9.5 at 25° C.

Using another 10 L of the substrate solution shown in Table 6, the same operations as described above were performed to yield 1.45 kg (moisture content: 7.2%) of L-aspartic acid crystals. The purity of the resultant crystals was 99.7%. Likewise, the mother liquor and the washing liquid were combined, and 170 g of fumaric acid was added thereto. This mixture was condensed, thereafter 25% aqueous ammonia was added to the mixture to adjust the pH to 9.5 at 25° C. Then, water was added thereto to make the total weight 11.1 kg. This liquid was combined with the re-prepared solution described above, kept in a thermostatic water bath of 20° C., fed to a column packed with the above-described transformant-immobilized aspartase through a Teflon tube covered with a heat insulator at a rate of 5 L/hr (LHSV=10.0) and circulated to perform a continuous reaction. The reaction solution was analyzed one hour after the start of the reaction. The results showed that L-aspartic acid was produced as a reaction product in an amount almost equimolar to that of the consumed fumaric acid, and that the ratio of conversion into L-aspartic acid was 99.7%. Using 10 L of this reaction solution, the same operations as described above were performed to yield 1.69 kg (moisture content: 7.1%) of L-aspartic acid crystals. The purity of the resultant crystals was 99.7%. These operations were repeated further; the reaction solution of 20 L (taken as 1 unit) was re-prepared and used 5 times. The results are shown in Table 7 below.

TABLE 5

| Crystallization | $1^{st}$ Time | $2^{nd}$ Time | $3^{rd}$ Time | $4^{th}$ Time | $5^{th}$ Time |
|---|---|---|---|---|---|
| Conversion ratio (%) | 99.7 | 99.7 | 99.7 | 99.7 | 99.7 |
| Wet L-aspartic acid crystals (kg) | 3.37 | 3.38 | 3.39 | 3.36 | 3.37 |
| Moisture content (%) | 7.1 | 7.2 | 7.0 | 7.1 | 7.0 |
| Dry weight (kg) | 3.13 | 3.14 | 3.15 | 3.12 | 3.137 |
| Purity (%) | 99.7 | 99.7 | 99.7 | 99.6 | 99.7 |
| Crystal form | needle-like | needle-like | needle-like | needle-like | needle-like |

Note: The values given above are calculated against 1 unit (i.e. 20 L) of reaction solution.

EXAMPLE 4

The transformant-immobilized aspartase prepared in Preparation Example 1 was dipped in 20% ammonium fumarate solution (pH 8.3) overnight. Subsequently, 500 ml of the resultant aspartase was packed in a column, outside of which was then covered with a heat insulator made of polystyrene foam to thereby insulate the reactor thermally. To this column, the substrate solution (shown in Table 4) retained at 20° C. in a thermostatic water bath of 20° C. was fed through a Teflon tube covered with a heat insulator at a rate of 5 L/hr (LHSV=10.0) and circulated to perform a continuous reaction.

The reaction solution was analyzed one hour after the start of the reaction. The results showed that L-aspartic acid was produced as a reaction product in an amount almost equimolar to that of the consumed fumaric acid, and that the ratio of conversion into L-aspartic acid was 99.2%.

Ten liters of this reaction solution (weight: 11.1 kg) was placed in a 20 L flask which was provided with a cooling tube so that pressure reduction and reflux can be carried out. The solution was heated to 95° C. When 1.00 kg of fumaric acid was added thereto and agitated, the fumaric acid crystals were completely dissolved. The agitation was continued further for about 3 minutes. Then, L-aspartic acid crystals began to deposit. After the liquid temperature was kept at 95° C. for 30 min, the pressure inside the flask was reduced at a rate of 15 torr/min. In the course of this operation, the liquid containing L-aspartic acid crystals began to boil at around 600 torr, thereafter the pressure was reduced while condensing the evaporated water in the cooling tube and returning it to the flask (average cooling rate: 0.71° C./min). After the pressure was reduced to 400 torr at which the liquid temperature was 78° C., the pressure was further reduced at a rate of 5 torr/min. About 1.5 hours thereafter, the pressure inside the flask was returned to ambient atmospheric pressure because the temperature of the liquid containing L-aspartic acid crystals reached 40° C. at 50 torr (average cooling rate: 0.54° C./min). Under these conditions, agitation was continued for 30 min to complete the deposition of L-aspartic acid crystals. The thus deposited L-aspartic acid crystals were separated through a centrifugal filter and washed with 1 L of water. The resultant L-aspartic acid crystals were 1.86 kg in weight (moisture content: 7.0%). After drying, the crystals had a weight of 1.73 kg and a purity of 99.7%. As to their form, they were mainly needle-like crystals 500 μm in average length. The above-described crystallization operations for L-aspartic acid were performed again, and the crystallized L-aspartic acid was separated by centrifugal filtration and washed with 500 ml of water. The resultant L-aspartic acid crystals were 1.88 kg in weight (moisture content: 7.1%); after drying, the crystals had a weight of 1.75 kg and a purity of 99.6%. When the amount of washing water was reduced to 250 ml in the above procedures, the resultant L-aspartic acid crystals were 1.86 kg in weight (moisture content: 7.0%); after drying, they had a weight of 1.73 kg and a purity of 99.5%. When the amount of washing water was reduced to 125 ml in the above procedures, the resultant L-aspartic acid crystals were 1.85 kg in weight (moisture content: 7.2%); after drying, they had a weight of 1.72 kg and a purity of 99.4%. When crystallization of L-aspartic acid was performed in the same manner as described above except that no washing was carried out with water, the resultant L-aspartic acid crystals were 1.98 kg in weight (moisture content: 7.2%); after drying, they had a weight of 1.75 kg and a purity of 98.9%.

EXAMPLE 5

The transformant-immobilized aspartase prepared in Preparation Example 1 was dipped in 20% ammonium fumarate solution (pH 8.3) overnight. Subsequently, 500 ml of the resultant aspartase was packed in a column, outside of which was then covered with a heat insulator made of polystyrene foam to thereby insulate the reactor thermally. To this column, the substrate solution (shown in Table 4) retained at 20° C. in a thermostatic water bath of 20° C. was fed through a Teflon tube covered with a heat insulator at a rate of 5 L/hr (LHSV=10.0) and circulated to perform a continuous reaction.

The reaction solution was analyzed one hour after the start of the reaction. The results showed that L-aspartic acid was produced as a reaction product in an amount almost equimolar to that of the consumed fumaric acid, and that the ratio of conversion into L-aspartic acid was 99.2%.

Ten liters of this reaction solution (weight: 11.1 kg) was placed in a 20 L flask which was provided with a cooling tube so that pressure reduction and reflux could be carried out. The solution was heated to 95° C. When 1.00 kg of fumaric acid was added thereto and agitated, the fumaric acid crystals were completely dissolved. The agitation was continued further for about 3 minutes. Then, L-aspartic acid crystals began to deposit. After the liquid temperature was kept at 95° C. for 30 min, the pressure inside the flask was reduced at a rate of 15 torr/min. In the course of this operation, the liquid containing L-aspartic acid crystals began to boil at around 600 torr, thereafter the pressure was reduced while condensing the evaporated water in the cooling tube and returning it to the flask (average cooling rate: 0.71° C./min). After the pressure was reduced to 400 torr at which the liquid temperature was 78° C. the pressure was further reduced at a rate of 10 torr/min. About 1 hour thereafter, the pressure inside the flask was returned to ambient atmospheric pressure because the temperature of the liquid containing L-aspartic acid crystals reached 40° C. at 50 torr (average cooling rate: 1.09° C./min). Under these conditions, agitation was continued for 30 minutes to complete the deposition of L-aspartic acid crystals. The thus deposited L-aspartic acid crystals were separated through a centrifugal filter and washed with 1 L of water The resultant L-aspartic acid crystals were 1.86 kg in weight (moisture content: 7.0%). After drying, the crystals had a weight of 1.73 kg and a purity of 99.7%. The above-described crystallization operations for L-aspartic acid were performed again, and the liquid containing L-aspartic acid crystals was cooled to 35° C. The crystallized L-aspartic acid was separated by centrifugal filtration and washed with 1 L of water. The resultant L-aspartic acid crystals were 1.95 kg in weight (moisture content: 7.0%); after drying, the crystals bad a weight of 1.81 kg and a purity of 99.7%. When the liquid containing L-aspartic acid crystals was cooled to 30° C. in the above-described procedures, the L-aspartic acid crystals after centrifugal filtration were 1.99 kg in weight (moisture content: 7.1%); after drying, the crystals had a weight of 1.85 kg and a purity of 99.1%.

EXAMPLE 6

The transformant-immobilized aspartase prepared in Preparation Example 1 was dipped in 20% ammonium fumarate solution (pH 8.3) overnight. Subsequently, 500 ml of the resultant aspartase was packed in a column, outside of which was then covered with a heat insulator made of polystyrene foam to thereby insulate the reactor thermally. To this column, the substrate solution (shown in Table 4) retained at 20° C. in a thermostatic water bath of 20° C. was fed through a Teflon tube covered with a heat insulator at a rate of 5 L/hr (LHSV=10.0) and circulated to perform a continuous reaction.

The reaction solution was analyzed one hour after the start of the reaction. The results showed that L-aspartic acid was produced as a reaction product in an amount almost equimolar to that of the consumed fumaric acid, and that the ratio of conversion into L-aspartic acid was 99.2%.

Five liters of this reaction solution was placed in a flask and heated to 95° C. In a separate vessel, 500 g of fumaric acid and 500 g of water were mixed together to prepare a slurry, which was heated to 95° C. The reaction solution and this slurry were independently fed to a reactor with a pump through a silicone tube at flow rates of 1110 g/min and 200 g/min, respectively. These two fluids were mixed at a three-forked joint and then introduced into 2 static mixers provided with a jacket (Noritake; Model 1/4(1)-N40-174-0; with a jacket; made of glass; 5 mm in inside diameter×325 mm in length; number of elements; 24) connected in series (see FIG. 1). In the jacket, hot water of 95° C. was circulated. At that time, the linear velocity of the fluid in the static mixers was about 1.1 m/sec. The above-described two fluids were mixed in the first static mixer to generate a homogeneous solution in which neither fumaric acid crystals nor L-aspartic acid crystals were present. The residence time of this solution in the static mixers was about 0.5 seconds. This solution was introduced into a 10 L flask which was provided with a cooling tube so that pressure reduction and reflux could be carried out, and the solution was agitated continuously. About 5 minutes later, L-aspartic acid crystals began to deposit. When 4 L of the solution had been introduced into the flask, the introduction was stopped. Thereafter, the pressure inside the flask was reduced at a rate of 15 torr/min. In the course of this operation, the liquid containing L-aspartic acid crystals began to boil at around 600 torr, thereafter the pressure was reduced while condensing the evaporated water in the cooling tube and returning it to the flask (average cooling rate: 0.71° C./min). After the pressure was reduced to 400 torr at which the liquid temperature was 79° C., the pressure was further reduced at a rate of 10 torr/min. About 1 hour thereafter, the pressure inside the flask was returned to ambient atmospheric pressure because the temperature of the liquid containing L-aspartic acid crystals reached 40° C. at 50 torr (average cooling rate: 1.08° C./min). Under these conditions, agitation was continued for 30 minutes to complete the deposition of L-aspartic acid crystals. The liquid containing L-aspartic acid crystals was cooled to 40° C. The crystals were separated by centrifugal filtration and washed with 100 ml of water. The resultant L-aspartic acid crystals were 753 g in weight (moisture content: 7.0%); after drying, the crystals had a weight of 700 g and a purity of 99.7%. As to their form, they were mainly needle-like crystals 500 μm in average length.

EXAMPLE 7

The transformant-immobilized aspartase prepared in Preparation Example 1 was dipped in 20% ammonium fumarate solution (pH 8.3) overnight. Subsequently, 500 ml of the resultant aspartase was packed in a column, outside of which was then covered with a heat insulator made of polystyrene foam to thereby insulate the reactor thermally. To this column, the substrate solution (shown in Table 4) retained at 20° C. in a thermostatic water bath of 20° C. was fed through a Teflon tube covered with a heat insulator at a rate of 5 L/hr (LHSV=10.0) and circulated to perform a continuous reaction.

The reaction solution was analyzed one hour after the start of the reaction. The results showed that L-aspartic acid was produced as a reaction product in an amount almost equimolar to that of the consumed fumaric acid, and that the ratio of conversion into L-aspartic acid was 99.2%.

Ten liters of this reaction solution (weight: 11.1 kg) was placed in a 20 L flask which was provided with a cooling tube so that pressure reduction and reflux could be carried out. The solution was heated to 95° C. When 1.00 kg of fumaric acid was added thereto and agitated, the fumaric acid crystals were completely dissolved. After the solution became homogeneous, the pressure inside the flask was reduced at a rate of 20 torr/min. As a result, L-aspartic acid crystals began to deposit immediately and the liquid began to boil violently, thereafter the pressure was further reduced while condensing the evaporated water in the cooling tube and returning it to the flask. About 40 minutes thereafter, the pressure inside the flask was returned to ambient atmospheric pressure because the temperature of the liquid containing L-aspartic acid crystals reached 40° C. at 50 torr (average cooling rate: 1.55° C./min). Under these conditions, agitation was continued for 30 minutes to complete the deposition of L-aspartic acid crystals. The thus deposited L-aspartic acid crystals were separated through a centrifugal filter and washed with 1 L of water. The resultant L-aspartic acid crystals were 2.18 kg in weight (moisture content: 24%); after drying, the crystals had a weight of 1.66 kg and a purity of 98.8%. As to their form, they were mainly needle-like crystals 30 μm in average length.

These L-aspartic acid crystals were suspended in 10 L of water, agitated and subjected to centrifugal filtration for separation. The resultant L-aspartic acid crystals were 2.14 kg in weight (moisture content: 23%); after drying, the crystals had a weight of 1.65 kg and a purity of 99.7%.

EXAMPLE 8

The transformant-immobilized aspartase prepared in Preparation Example 1 was dipped in 20% ammonium fumarate solution (pH 8.3) overnight. Subsequently, 500 ml of the resultant aspartase was packed in a column, outside of which was then covered with a heat insulator made of polystyrene foam to thereby insulate the reactor thermally. To this column, the substrate solution (shown in Table 4) retained at 20° C. in a thermostatic water bath of 20° C. was fed through a Teflon tube covered with a heat insulator at a rate of 5 L/hr (LHSV=10.0) and circulated to perform a continuous reaction.

The reaction solution was analyzed one hour after the start of the reaction. The results showed that L-aspartic acid was produced as a reaction product in an amount almost equimolar to that of the consumed fumaric acid, and that the ratio of conversion into L-aspartic acid was 99.2%.

Five liters of this reaction solution was placed in a flask and heated to 95° C. The reaction solution was fed to a reactor with a pump through a silicone tube at flow rates of 1110 g/min. To this reactor, fumaric acid containing 5% of water was fed continuously at the rate of 105 g/min through a powder feeder. The resultant fluid was introduced into 2 static mixers provided with a jacket (Noritake) connected in series and mixed as described in Example 6. In the jacket, hot water of 95° C. was circulated. At the exit of the static mixer, a homogeneous solution was generated in which neither fumaric acid crystals nor L-aspartic acid crystals were present. This solution was introduced into a 10 L flask which was provided with a cooling tube so that pressure reduction and reflux could be carried out, and the solution was agitated continuously. About 10 minutes later, L-aspartic acid crystals began to deposit. When 4 L of the solution had been introduced into the flask, the introduction was stopped. Thereafter, the pressure inside the flask was reduced at a rate of 15 torr/min. In the course of this operation, the liquid containing L-aspartic acid crystals began to boil at around 600 torr. thereafter the pressure was reduced while condensing the evaporated water in the cooling tube and removing it out of the system (average cooling rate: 0.67° C./min). After the pressure was reduced to 400 torr at which the liquid temperature was 79° C., the pressure was further reduced at a rate of 10 torr/min. About 1 hour thereafter, the pressure inside the flask was returned to ambient atmospheric pressure because the temperature of the liquid containing L-aspartic acid crystals reached 50° C. at 150 torr (average cooling rate: 1.16° C./min). Under these conditions, agitation was continued for 10 minutes to complete the deposition of L-aspartic acid crystals. The crystals were separated by centrifugal filtration and washed with 100 ml of water. The resultant L-aspartic acid crystals were 760 g in weight (moisture content: 8.0%); after drying, the crystals had a weight of 699 g and a purity of 99.6%. As to their form, they were mainly needle-like crystals 300 μm in average length.

EXAMPLE 9

L-aspartic acid was produced using a continuous crystallizer as shown in FIG. 2.

Two kilograms of fumaric acid and 2 kg of water were placed in a 10 L separable flask (A) equipped with an agitator to prepare a 50% by weight fumaric acid slurry. The same aqueous ammonium L-aspartate solution after reaction as used in Example 6 was placed in a 20 L plastic tank (B). This solution and the above slurry were led from these two containers through stainless pipes of about 5 m (E and F) dipped in a bath of 100° C. using pumps (C and D), respectively. The flow rates of the feeding were 28.4 g/min for the fumaric acid slurry and 157 g/min for the aqueous ammonium L-aspartate solution.

These two liquids were combined and introduced into a line mixer (G) equipped with a jacket in which a heat medium of 95° C. was circulating. The liquid at the exit of this line mixer was in a homogeneously dissolved state in which neither fumaric acid crystals nor L-aspartic acid crystals were present. The liquid temperature was about 90° C. This homogeneous solution was introduced into a 10 L separable flask (H) with an agitator. The pressure inside the flask was reduced to 50 torr in advance. The moisture content of the solution introduced therein was evaporated to thereby cool the solution by means of the heat of evaporation. Thus, crystallization was performed. At that time, the water condensed in a condenser (I) was not returned to the separable flask (H) but introduced into a receiver (J). One hour thereafter, the 10 L separable flask became almost full of the crystallization slurry. Then, it was started to draw out the slurry from the flask into a slurry-drawing out vessel (K) in which the pressure was reduced to 30 torr in advance, utilizing the pressure difference. The drawing out of slurry was performed in such a manner that the level of liquid surface in the separable flask (H) was maintained constant. Under these conditions, crystallizing operations were continued further for 1 hour. One hour thereafter, since the slurry-drawing out vessel (K) became full, the feeding of the 50% fumaric acid slurry was stopped first, and then the feeding of the aqueous ammonium L-aspartate solution was stopped. The pressure inside the 10 L separable flask was returned to ambient pressure, and the slurry containing L-aspartic acid crystals was drawn out. Two slurries (1100 g each) from the separable flask (H) and from the slurry-drawing out vessel (K) were subjected to centrifugal filtration separately. The resultant filtration cakes were washed separately with 50 ml of water to obtain 190 g and 193 g of wet L-aspartic acid crystals, respectively. Both of these crystals had a purity of 99.6% by weight (excluding moisture).

Comparative Example 1

The transformant-immobilized aspartase prepared in Preparation Example 1 was dipped in 20% ammonium fumarate solution (pH 8.3) overnight. Subsequently, 500 ml of the resultant aspartase was packed in a column, outside of which was then covered with a heat insulator made of polystyrene foam to thereby insulate the reactor thermally. To this column, the substrate solution (shown in Table 4) retained at 20° C. in a thermostatic water bath of 20° C. was fed through a Teflon tube covered with a heat insulator at a rate of 5 L/hr (LHSV=10.0) and circulated to perform a continuous reaction.

The reaction solution was analyzed one hour after the start of the reaction. The results showed that L-aspartic acid was produced as a reaction product in an amount almost equimolar to that of the consumed fumaric acid, and that the ratio of conversion into L-aspartic acid was 99.2%.

Ten liters of this reaction solution (weight: 11.1 kg) was placed in a 20 L flask, to which 1.00 kg of fumaric acid was added and agitated at 30° C. As a result, a heterogeneous slurry was generated in which crystals were constantly present. After agitation had been continued for 30 minutes, L-aspartic acid crystals deposited were separated with a centrifugal filter and washed with 1 L of water. The resultant L-aspartic acid crystals were 2.33 kg in weight (moisture content: 24.0%); after drying, the crystals had a weight of 1.77 kg and a purity of 98.2%. As to their form, they were mainly extremely small crystals of indeterminate forms 10 μm or less in size or such crystals associated together.

These L-aspartic acid crystals were suspended in 10 L of water, agitated and subjected to centrifugal filtration for separation. The resultant L-aspartic acid crystals were 2.08 kg in weight (moisture content: 22.0%); after drying, the crystals had a weight of 1.62 kg and a purity of 99.2%.

Comparative Example 2

The transformant-immobilized aspartase prepared in Preparation Example 1 was dipped in 20% ammonium fumarate solution (pH 8.3) overnight. Subsequently, 500 ml of the resultant aspartase was packed in a column, outside of which was then covered with a heat insulator made of polystyrene foam to thereby insulate the reactor thermally. To this column, the substrate solution (shown in Table 4) retained at 20° C. in a thermostatic water bath of 20° C. was fed through a Teflon tube covered with a heat insulator at a rate of 5 L/hr (LHSV=10.0) and circulated to perform a continuous reaction.

The reaction solution was analyzed one hour after the start of the reaction. The results showed that L-aspartic acid was produced as a reaction product in an amount almost equimolar to that of the consumed fumaric acid, and that the ratio of conversion into L-aspartic acid was 99.2%.

Ten liters of this reaction solution (weight: 11.1 kg) was placed in a 20 L flask which was provided with a cooling tube so that pressure reduction and reflux could be carried out. The solution was heated to 95° C. When 1.00 kg of fumaric acid was added thereto and agitated, the fumaric acid crystals were completely dissolved. When the agitation was continued further for about 3 minutes, L-aspartic acid crystals began to deposit. The liquid temperature was raised to 95° C., at which the liquid was retained for 30 minutes. Then, the pressure inside the flask was reduced at a rate of 15 torr/min. In the course of this operation, the liquid containing L-aspartic acid crystals began to boil at around 600 torr, thereafter the pressure was reduced while condensing the evaporated water in the cooling tube and returning it to the flask (average cooling rate: 0.71° C./min). After the pressure was reduced to 400 torr at which the liquid temperature was 78° C., the pressure was further reduced at a rate of 3 torr/min. After about 2 hours and a half, the pressure inside the flask was returned to ambient atmospheric pressure because the temperature of the liquid containing L-aspartic acid crystals reached 20° C. (average cooling rate: 0.9° C./min). Under these conditions, agitation was continued for 30 minutes to complete the deposition of L-aspartic acid crystals. The thus deposited L-aspartic acid crystals were separated through a centrifugal filter and washed with 1 L of water. The resultant L-aspartic acid crystals were 2.10 kg in weight (moisture content: 12%); after drying, the crystals had a weight of 1.84 kg and a purity of 98.5%.

All publications, patents and patent applications cited herein are incorporated herein by reference in their entirety.

The following are information on sequences described herein:

SEQUENCE INFORMATION

What is claimed is:

1. A method for producing L-aspartic acid comprising:
   treating an ammonium fumarate solution, which consists essentially of ammonium fumarate and water, with aspartase to generate an ammonium L-aspartate solution;
   heating the ammonium L-aspartate solution to a temperature within the range of 50 to 130° C.;
   adding fumaric acid in the form of dry crystals, moisture-containing crystals, or an aqueous suspension to the heated ammonium L-aspartate solution in a molar ratio of 0.4 to 0.8 to the total molar amount of ammonium L-aspartate and ammonium fumarate contained in the ammonium L-aspartate solution to form a resultant mixture and applying a shearing force to the resultant mixture, while maintaining the temperature between 50° C. and 130° C. to obtain a homogenous solution;
   cooling the homogenous solution at a rate of 0.1 to 5° C. per minute to between 25 and 100° C., thereby obtaining a suspension containing L-aspartic acid; and
   separating L-aspartic acid crystals from the suspension.

2. The method according to claim 1, wherein the cooling is performed by evaporating water under reduced pressure; condensing evaporated water by cooling through a condenser; and either returning the condensed water to a reactor for L-aspartic acid crystallization or removing the condensed water.

3. The method according to claim 2, wherein pressure reduction at the time of cooling under reduced pressure is performed at a rate of 1–20 torr per minute from a range of pressure 10–200 torr higher than the vapor pressure at which the solution to be cooled begins to boil.

4. The method according to claim 1, wherein the homogenous solution is further maintained at 50 to 130° C. for 0.1 second to 1 hour.

5. The method according to claim 1, wherein the shearing force is applied by mixing the resultant mixture continuously.

6. The method according to claim 1, wherein the separating step is performed by filtration.

7. The method according to claim 6, wherein the mother liquor obtained by the filtration is used as a source of ammonium fumarate.

8. The method according to claim 7, wherein the mother liquor is used repeatedly.

9. The method according to claim 1, further comprising washing the L-aspartic acid crystals obtained in the separating step with water.

10. The method according to claim 9, wherein washing liquid obtained after washing is used as a source of ammonium fumarate.

* * * * *

```
                          SEQUENCE LISTING

<160> NUMBER OF SEQ ID NOS:  3

<210> SEQ ID NO 1
<211> LENGTH: 1573
<212> TYPE: DNA
<213> ORGANISM: Artificial Sequence
<220> FEATURE:
<223> OTHER INFORMATION: Description of Artificial Sequence:cDNA to
      mRNA of aspartase gene derived from Escherichia coli K-12
<221> NAME/KEY: CDS
<222> LOCATION: (91)..(1524)

<400> SEQUENCE: 1
ggggataatc gtcggtcgaa aacattcga aaccacatat attctgtgtg tttaaagcaa      60
atcattggca gcttgaaaaa gaaggttcac atg tca aac aac att cgt atc gaa    114
                                 Met Ser Asn Asn Ile Arg Ile Glu
                                   1               5 gaa gat ctg ttg ggt acc agg gaa gtt cca gct gat gcc tac tat ggt     162
Glu Asp Leu Leu Gly Thr Arg Glu Val Pro Ala Asp Ala Tyr Tyr Gly
         10                  15                  20 gtt cac act ctg aga gcg att gta aac ttc tat atc agc aac aac aaa     210
Val His Thr Leu Arg Ala Ile Val Asn Phe Tyr Ile Ser Asn Asn Lys
 25                  30                  35                  40 atc agt gat att cct gaa ttt gtt cgc ggt atg gta atg gtt aaa aaa     258
Ile Ser Asp Ile Pro Glu Phe Val Arg Gly Met Val Met Val Lys Lys
                 45                  50                  55 gcc gca gct atg gca aac aaa gag ctg caa acc att cct aaa agt gta     306
Ala Ala Ala Met Ala Asn Lys Glu Leu Gln Thr Ile Pro Lys Ser Val
             60                  65                  70 gcg aat gcc atc att gcc gca tgt gat gaa gtc ctg aac aac gga aaa     354
Ala Asn Ala Ile Ile Ala Ala Cys Asp Glu Val Leu Asn Asn Gly Lys
         75                  80                  85 tgc atg gat cag ttc ccg gta gac gtc tac cag ggc ggc gca ggt act     402
Cys Met Asp Gln Phe Pro Val Asp Val Tyr Gln Gly Gly Ala Gly Thr
 90                  95                 100 tcc gta aac atg aac acc aac gaa gtg ctg gcc aat atc ggt ctg gaa     450
Ser Val Asn Met Asn Thr Asn Glu Val Leu Ala Asn Ile Gly Leu Glu
105                 110                 115                 120 ctg atg ggt cac caa aaa ggt gaa tat cag tac ctg aac ccg aac gac     498
Leu Met Gly His Gln Lys Gly Glu Tyr Gln Tyr Leu Asn Pro Asn Asp
                125                 130                 135 cat gtt aac aaa tgt cag tcc act aac gac gcc tac ccg acc ggt ttc     546
His Val Asn Lys Cys Gln Ser Thr Asn Asp Ala Tyr Pro Thr Gly Phe
            140                 145                 150 cgt atc gca gtt tac tct tcc ctg att aag ctg gta gat gcg att aac     594
Arg Ile Ala Val Tyr Ser Ser Leu Ile Lys Leu Val Asp Ala Ile Asn
        155                 160                 165 caa ctg cgt gaa ggc ttt gaa cgt aaa gct gtc gaa ttc cag gac atc     642
Gln Leu Arg Glu Gly Phe Glu Arg Lys Ala Val Glu Phe Gln Asp Ile
    170                 175                 180 ctg aaa atg ggt cgt acc cag ctg cag gac gca gta ccg atg acc ctc     690
Leu Lys Met Gly Arg Thr Gln Leu Gln Asp Ala Val Pro Met Thr Leu
185                 190                 195                 200 ggt cag gaa ttc cgc gct ttc agc atc ctg ctg aaa gaa gaa gtg aaa     738
Gly Gln Glu Phe Arg Ala Phe Ser Ile Leu Leu Lys Glu Glu Val Lys
                205                 210                 215 aac atc caa cgt acc gct gaa ctg ctg ctg gaa gtt aac ctt ggt gca     786
Asn Ile Gln Arg Thr Ala Glu Leu Leu Leu Glu Val Asn Leu Gly Ala
```

```
aca gca atc ggt act ggt ctg aac acg ccg aaa gag tac tct ccg ctg      834
Thr Ala Ile Gly Thr Gly Leu Asn Thr Pro Lys Glu Tyr Ser Pro Leu
            235                 240                 245 gca gtg aaa aaa ctg gct gaa gtt act ggc ttc cca tgc gta ccg gct      882
Ala Val Lys Lys Leu Ala Glu Val Thr Gly Phe Pro Cys Val Pro Ala
        250                 255                 260 gaa gac ctg atc gaa gcg acc tct gac tgc ggc gct tat gtt atg gtt      930
Glu Asp Leu Ile Glu Ala Thr Ser Asp Cys Gly Ala Tyr Val Met Val
265                 270                 275                 280 cac ggc gcg ctg aaa cgc ctg gct gtg aag atg tcc aaa atc tgt aac      978
His Gly Ala Leu Lys Arg Leu Ala Val Lys Met Ser Lys Ile Cys Asn
                285                 290                 295 gac ctg cgc ttg ctc tct tca ggc cca cgt gcc ggc ctg aac gag atc     1026
Asp Leu Arg Leu Leu Ser Ser Gly Pro Arg Ala Gly Leu Asn Glu Ile
            300                 305                 310 aac ctg ccg gaa ctg cag gcg ggc tct tcc atc atg cca gct aaa gta     1074
Asn Leu Pro Glu Leu Gln Ala Gly Ser Ser Ile Met Pro Ala Lys Val
        315                 320                 325 aac ccg gtt gtt ccg gaa gtg gtt aac cag gta tgc ttc aaa gtc atc     1122
Asn Pro Val Val Pro Glu Val Val Asn Gln Val Cys Phe Lys Val Ile
330                 335                 340 ggt aac gac acc act gtt acc atg gca gca gaa gca ggt cag ctg cag     1170
Gly Asn Asp Thr Thr Val Thr Met Ala Ala Glu Ala Gly Gln Leu Gln
345                 350                 355                 360 ttg aac gtt atg gag ccg gtc att ggc cag gcc atg ttc gaa tcc gtt     1218
Leu Asn Val Met Glu Pro Val Ile Gly Gln Ala Met Phe Glu Ser Val
                365                 370                 375 cac att ctg acc aac gct tgc tac aac ctg ctg gaa aaa tgc att aac     1266
His Ile Leu Thr Asn Ala Cys Tyr Asn Leu Leu Glu Lys Cys Ile Asn
            380                 385                 390 ggc atc act gct aac aaa gaa gtg tgc gaa ggt tac gtt tac aac tct     1314
Gly Ile Thr Ala Asn Lys Glu Val Cys Glu Gly Tyr Val Tyr Asn Ser
        395                 400                 405 atc ggt atc gtt act tac ctg aac ccg ttc atc ggt cac cac aac ggt     1362
Ile Gly Ile Val Thr Tyr Leu Asn Pro Phe Ile Gly His His Asn Gly
410                 415                 420 gac atc gtg ggt aaa atc tgt gcc gaa acc ggt aag agt gta cgt gaa     1410
Asp Ile Val Gly Lys Ile Cys Ala Glu Thr Gly Lys Ser Val Arg Glu
425                 430                 435                 440 gtc gtt ctg gaa cgc ggt ctg ttg act gaa gcg gaa ctt gac gat att     1458
Val Val Leu Glu Arg Gly Leu Leu Thr Glu Ala Glu Leu Asp Asp Ile
                445                 450                 455 ttc tcc gta cag aat ctg atg cac ccg gct tac aaa gca aaa cgc tat     1506
Phe Ser Val Gln Asn Leu Met His Pro Ala Tyr Lys Ala Lys Arg Tyr
            460                 465                 470 act gat gaa agc gaa cag taatcgtaca gggtagtaca aataaaaaag            1554
Thr Asp Glu Ser Glu Gln
                475 gcacgtcaga tgacgtgcc                                                1573
```

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide based on aspartase gene derived
      from Escherichia coli K-12

<400> SEQUENCE: 2

```
ggataatcgt cggtcgaaaa                                              20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:Designed
      oligonucleotide based on aspartase gene derived
      from Escherichia coli K-12

<400> SEQUENCE: 3
cgtcatctga cgtgcctt                                                19
```